United States Patent [19]

Nauta et al.

[11] Patent Number: 6,143,525
[45] Date of Patent: Nov. 7, 2000

[54] COMPLEX INDUCIBLE PROMOTER SYSTEM DERIVABLE FROM A PHAGE OF A LACTIC ACID BACTERIUM (LAB), AND ITS USE IN A LAB FOR PRODUCTION OF A DESIRED PROTEIN

[75] Inventors: Arjan Nauta, Groningen; Gerard Venema, Haren; Jan Kok, Groningen; Adrianus Marinus Ledeboer, Rotterdam, all of Netherlands

[73] Assignee: Quest International B.V., Naarden, Netherlands

[21] Appl. No.: 08/737,226

[22] PCT Filed: May 12, 1995

[86] PCT No.: PCT/NL95/00172

§ 371 Date: Apr. 3, 1997

§ 102(e) Date: Apr. 3, 1997

[87] PCT Pub. No.: WO95/31563

PCT Pub. Date: Nov. 23, 1995

[30] Foreign Application Priority Data

May 12, 1994 [EP] European Pat. Off. ............. 94201355

[51] Int. Cl.$^7$ ...................................................... C12P 21/04
[52] U.S. Cl. ...................... 435/71.2; 435/69.1; 435/71.1; 435/252.3; 435/320.1; 536/24.1
[58] Field of Search .................................. 435/69.1, 320.1, 435/172.3, 71.1, 71.2, 252.3; 536/24.1

[56] References Cited

FOREIGN PATENT DOCUMENTS

WO 92/04451 3/1992 WIPO .
WO 93/17117 9/1993 WIPO .

OTHER PUBLICATIONS van der Vossen et al, Applied and Environmental Microbiology, vol. 53, No. 10, pp. 2452–2457 (Oct. 1987).
Platteeuw et al, Applied and Environmental Microbiology, vol. 60, No. 2, pp. 587–593 (Feb. 1994).
Lakshmidevi et al, Applied and Environmental Microbiology, vol. 56, No. 4, pp. 934–942 (Apr. 1990).
van de Guchte et al, Gene, 144 (1994) 93–95.
Achen et al, Gene, 45 (1986) 45–59.
Kim et al, Food Microbiology, 8 (1991) 27–36.
van de Guchte et al, FEMS Microbiology Reviews, 88 (1992) 73–92.

*Primary Examiner*—Remy Yucel
*Attorney, Agent, or Firm*—Pillsbury Madison & Sutro LLP

[57] ABSTRACT

The invention provides a complex inducible promoter system from a phage of a lactic acid bacterium, especially one having the DNA sequence of SEQ. ID. No: 3 given in FIG. 2, or a DNA sequence essentially corresponding to those sequences, and a modification of (an essential part of) such promoter system in which the mitomycin C induction system is replaced by a good-grade system, e.g. a temperature-initiated induction system or a salt-initiated induction system. Also is provided a recombinant vector and a transformed lactic acid bacterium comprising (an essential part of) such promoter system. Further a process for producing a desired protein by such transformed bacterium is provided, comprising expressing a gene encoding said desired protein or a precursor thereof under control of such promoter system or an essential part thereof. Preferably, the transformed lactic acid bacterium is made food-grade due to using food-grade DNA sequences and/or removing non-food-grade DNA sequences. When required, the desired protein can be secreted by the lactic acid bacterium if a DNA sequence fused to the gene encoding the desired protein is present which effects secretion of the desired protein or its precursor. The process can be used in a fermentation process, in which the desired protein causes lysis of the bacterial cells so that the contents of the cells can be released, or in which the desired protein is an enzyme involved in flavour formation, or in which the desired protein has a function in a cheese production process, such as chymosin or a precursor thereof, or an enzyme involved in flavour formation.

16 Claims, 7 Drawing Sheets

Fig. 1B

```
ACAATCCGAAGCACGGAGTACATGACGGATGCCGAAGCTT GCATGCCTGCAGGTC
T I R S T E Y M T D A K L   A C L Q V
            ORF 29 ->      -> pUC18 MCS
```

Fig. 2A

```
GACTCTAGAGTCGGG GCCGTCGTTTTACAACGTCGTGAC
D S R V G   A V V L Q R R D
               -> codon 9 of E.coli lacZ
```

HindIII
AAGCTTCGCCATCCGTCATGTACTCCGTCGTCTTCGGATTGTGTGGGAGGACTTCTTCATATACCAGCCAATCCTGAAATGGCTCAGCACTTGGCAATTACTTTCCCAGCTAATTGATAAGACC
TTCGAAGCGTAGGCAGTACATGAGGCAGCAAGCCTAACACCCTCCTGAAGAAGTATGGTTAGGACTTTACCGAGTCGTGAACCGTTAAATGAAAGCGGTCGATTAACTATTTCTGG
L K A D T M Y E T S R I T P L V E E Y V W D Q F P E A S P L K S E G A L Q Y L G AGGTTCTGAAATTACTGTGACACTTTGTACTCCTGAGGGGTCGTGATTCGCGACTCGTGTTATATTTGTCTTTTACATGAGATTTCAAAGCATCCTGAAATTCTTGTAACCAATAGC
TCCAAGACTTTAATGACACTGTGAAACATGATGAGGACACTCCCCAGCACTAAGGCTCCCCAGCACTGAGGAGAATATAAACAGAAAATGTACTCTAAAGTTTCGTAGGGACTTTAAGAACATTGGTTATCG
P E S I V T V S Q V G S P T T I R S E R K Y K D K V H S K L A D R F N K Y G I A
                                                      ORF 29 <--          RBS O₃

AATTGCTACATCTTTTCCGACAAACCAAGGTTCATCATTGATAAGTTCGTCGTACTGTAAGTTATTAAAATTAAAATTTTGTAATTCTTTCATGTTTTGCCTTTCTAACTAGCCAA
TTAACGATGTAGAAAAGGCTGTTTGGTTCCAAGTAACTATTCAAGCATGACATTCATGAAGCAGTTAATTTTTAATTTTAAACATTAAGAAAGTACAAAACGAAAGATTGATCGGTTA
I A V D K G V F W P E D N I L V T R V P L N N F N F N Q L E K M        *   S A L
                                                                              XbaI

TTGTCAAGTT TTTGATTAAAATTTTTCAGCACACAAAAATAACATCGGTTAAATCTGTAAATAACCTCTGCAATGTTCGTCGTCTGAAACAGCATCTATTCTAGATGGGTTGATACGCCAC
AACAGTTCAA AAACTAATTTTTAAAAAGTCGTGTTTTTATTGTAGCCAATTTAGATGAGTTATTGGAGACGTTACAAGCGACGACTTGTCGTAGATAAGATCTACCAACTATGCGGTG
K D L K Q N F N K L V F I V D L T D V G I V E A I N A A S V A D I R S P N I R W
                                                                        ORF 28 (tec) <--        RBS TTATAAAATGTGTATAGGGAACGTTAATTTTTTGCGATAAGTTTATACTTCATTCCTGAAGAGTCTAATAACTCATCAGTGGCTCATTAACTTGAGTAGATCACCGAGTATTGAGTGACGTTTAAAAAAGACGGTATGACCGAGGA
AATATTTTACAACATATCCCTTGCAATTAAAAAACGCTATTGAAATATGAAGTAAGACATCTCAGATTATTGAGTAGATCACCGAGTATTGAGTGACGTTTAAAAAAGACGGTATGACCGAGGA
K Y F T T Y P V N I K K A I V K Y K M G S S D L L E D L P E Y T K K E A M

Fig. 2B

TTCTGCCCCTCTGGGCTTTTTATTGCCAAACTTGCTACTTACATCGCGGTGATACGTCTCGTGTACGTCATTGAGCCTGTTCCGTCCGCCTACTGAATGCTCCATGATTGTCGCT
AAGACGGGAGACCCCGAAAAATAAACGGTTTGAACGATGAATGTAGCGCCACCTATGCAGCACATGGCAGTAAACTCGGACAAGCAGTAGCAGGCAGGCCATGACTTACGAGGTACTAACAAGCGA $O_1$                      $O_2$          -35                    $P_2$         -10
TGTTTGACTTTATGAATTATAATTATAACCTTTAACTATCAATTTGTCAAGTTAAACTTTCGAAATAGTACAAGTTTTGTTTGTTGTGCTATAATTAGTGTATGAAAAAATACGACTACCT
ACAAACTGAAATACTTAATTATATTGGAAATTGATAGTTAAACAGTTCAATTTGAAAGCTTTATCATGTTCAATTTGAAACAACAAACGATATTAATCACATACTTTTTTATGCTGATGGA
                        -10
                                                           -35
        RBS           --> ORF 27 (rro)                                          NcoI
                                          M K E F G E K L G K S E S A I S K W I K G V R S P M V GAAATGATAGATTATTTCAGAAAAGAGAATGGTTTGACGATGAAAGAGTTGGCGAAAGCTAGGAAATCTGAGTCAGCTATTTCGAAATGATAAAGGGTTAGAAGTCCCATGGTT
CTTTACTATCTAATAAAGTCTTTTCTCTTACCAAACTGCTACTTTCGATCCTTCAAACCGCTTTCGATCAGTCGATAAAGCTTTACTATTTTCCCCAATCTTCAGGGTACCAA
 E D F D K M V N L F N T D P E T L M Y G A S D L S T T L S E I N K I S S Q L E E GAAGATTTTGATAAAATGGTCAATCTATTCAATACTGATCCTGAGACATTAATGTATGGTGCTTCTGACCTTTCTACAACTCTATCCGAAATAAATCAGTTCAAGTGTTGAGCTTCTT
CTTCTAAAACTATTTTACCAGTTAGATAAGTTATGACTAGGACTCTGTAATTACATACCGAAGAGATGTTGAGATAGGCTTTATTTATTTTAGTCAAGTTCAACTCGAAGAA
 E D F D K M V N L F N T D P E T L M Y G A S D L S T T L S E I N K I S S Q L E E CCACGTCAGAAGTGTTTAAATACTGCAAATAATCAGTTAGATGAGCAAAACCAAGAAAAGGAATCTAAAGTGATTCCAATTAATAAATACCTGACGATTTACCACCATAT
GGTGCAGTCTTCAACAAATTTATGACGTTTATTAGTCAATCTACTCCGTTTGGTTCTTTCTTTTTCCTTAGATTTCACTAAGGTTAATTATTTTATGACTGCTAAATGTGGTATA
 P R Q K V V L N T A N N Q L D E Q N Q E K K K E S K V I P I N K I P D D L P P Y

Fig. 2C

```
ATAAGTAGAAAGATTTAGAGAATTTCGTTATGCCTACAAACACTATGAATGAGGCTGATGAAGATATGTTCCTATTCTTGTAGGATAGCGCCCGACTTCCTCTTGAT
TATTCATCTTTCTAAAATCTCTAAAGCAATACGGATGTTGTGATTACTCCGACTACTTCTATACCATCTACAAGGATAAGAACCATCTATCGCCGCCTGAAGGAGAACTA
 I  S  R  K  I  L  E  N  F  V  M  P  T  N  T  M  E  Y  E  A  D  E  D  M  V  D  V  P  I  L  G  R  I  A  A  G  L  P  L  D

GCAGTAGAAAACTTCGACGTGTACAAGACCAGTACCTGCGCACTTCTCTATCTTCTGCTCGTGATTACTATTGGTTAATGGTTGATGGGCATAGCATGGAACCGAAAATTCCATATGGAGCT
CGTCATCTTTTGAAGCTGCACATGTTCTGGTCATGGACGCGTCATGATAGAAGACGAGCACTAATGATAACCAATTACCAACTACCCGTATCGTACCTTGGCTTTTAAGGTATACCTCGA
 A  V  E  N  F  D  G  T  R  P  V  P  A  H  F  L  S  S  A  R  D  Y  Y  W  L  M  V  D  G  H  S  M  E  P  K  I  P  Y  G  A

TATGTTTTAATTGAAGCTGTTCCTGATGTGAGCGACGGTACTATTGGAGCTGTTCTTTTCCATGATGATTGTCAGGCAACATTAAAAAAAGTTTATCATGAAATAGATTGCTTGAGACTT
ATACAAAATTAACTTCGACAAGGACTACACTCGCTGCCATGATAACCTCGACAATTGGAACAAGAAAAGGTACTACTAACAGTCCGTTGTAATTTTTTCAAATAGTACTTTATCTAACGAACTCGAA
 Y  V  L  I  E  A  V  P  D  V  S  D  G  T  I  G  A  V  L  F  H  D  D  C  Q  A  T  L  K  K  V  Y  H  E  I  D  C  L  R  L
                                                              PvuII

GTGTCAATCAACAAAGAATTTAAGACCAATTTGCTACACAAGACAATCCAGCAGTCTGTGATTGGGCAAGCTGTCAAAGTAGAAATTGATTTATAATAAATATACGAGCAATGTCTTGA
CACAGTTAGTTGTTGTTTCTTAAATTCTGGTTAACGATGTGTTCTGTTAGGTCGTCGACACTGTTAGGGTCGTCAGATTTCATCTTTAACTAAATAATTATATGCTCGTTACAGAACT
 V  S  I  N  K  E  F  K  D  Q  F  A  T  Q  D  N  P  A  A  V  I  G  Q  A  V  K  V  E  I  D  L  *

TTCTCGTTAAAGCTAGGTTAGGAAAATATAAACATTATGAAAATGGAAAAACTCCTAAAGCTAAAAAACCAATTATAAAAGAATATGTTTTGATTGTTGTAGTAATCGTAGTAGCG
AAGAGCAATTTTCGATCCAATCCTTTATATTTGTAATACTTTTCTTGAGGATTTCGATTTTTGGTTAAATATATTTCTTATACCAAAACCTAACAACATCATTAGCATCATCGC
                                                     PvuII

GTTATTGGTAGCGCACTTGGAGGAGGAGGCAAAGGCAAAGTGGAACATCAACTTCTACATCCTCAAGTTCTAAAATTAAAACAGCTG
CAATAACCATCGCGTGAACCTCCTCCTCCGTTTCCGTTTCACCTTGTAGTTGAAGATGTAGGAGTTCAAGATTTTAATTTGTCGAC
```

Fig. 3

```
ORF 27    MKEFGEKLGKSESAISKWIKGVRSPMVEDFDKMVNLFNTDPETLMYGASD    50
DinR      MT----KLSKRQLDILRFIKA--EVKSKGYPPSVREIGE-----------    33
C1434     MS-----------ISSRVKSKRIQ-------------------LGLNQAE    20
             *            *    .*

ORF 27    LSTTLSEINKISSQLEEPRQKVVLNTANNQLDEQNQEKKKESKVIPINKI   100
DinR      -AVGLASSSTVHGHLA-------------RLETKGLIRRDPTKPRAIEIL    69
C1434     LAQKVGTTQQSIEQLENGKTK--------------------RPRFLPEL    49
           . .                *                        . . .

ORF 27    PDDLPPYISRKILENFVMPTNTMEYEADEDM-VDVPILGRIAAGLPLDA-   148
DinR      DEEVDI-------------------PQSQV-VNVPVIGKVTAGSPITA-    97
C1434     ASALGVSVDW-LLNG--TSDSNVRFVGHVEPKGKYPLISMVRAGSWCEAC    96
             .                          *..  . ** * *

ORF 27    ----VENFDGTRPVPAHFLSSARDYYWLMVDGHSM----EPKIPYGAYVL   190
DinR      ----VENIEEYFPLPDRMVPPDEHVFMLEIMGDSM---IDAGILDKDYVI   140
C1434     EPYDIKDIDEWYDSDVNLLGNG---FWLKVEGDSMTSPVGQSIPEGHMVL   143
               .     .        *  . * **    *        *   *.

ORF 27    IEAVPDVSDGTIGAVLFHDDCQATLKKVYHEIDCLRLVSINKEFKDQFAT   240
DinR      VKQQNTANNGEIVVAMTEDD-EATVKRFYKEDTHIRLQPENPTM-EPIIL   188
C1434     VDTGREPVNGSLVVAKLTDANERTFKKLVIDGGQKYLKGLNPSW--PMTP   191
              *   .   *    * *  *    * *     * *

ORF 27    QDNPAAVIGQAVKVEIDL-    258
DinR      QN--VSILGKVIGVFRTVH   205
C1434     INGNCKIIGVVVEARVKFV   210
              ..*    .
```

Fig. 4

| Protein | <----Helix----> | | | | | | | <-Turn-> | | | <---------Helix---------> | | | | | | | |
|---|---|---|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 | 16 | 17 | 18 | 19 | 20 |
| ORF 27 | M | K | E | F | G | E | K | L | G | K | S | E | S | A | I | S | K | W | I | K |
| ORF 28 | A | A | N | I | A | E | V | I | G | V | D | L | I | D | V | I | F | V | L | K |
| λ CII | T | E | K | T | A | E | A | V | G | V | D | K | S | Q | I | S | R | W | K | R |
| φ80 gp30 | H | K | V | L | A | E | K | V | G | V | T | P | Q | Q | A | I | N | M | L | K |
| P22 C2 | Q | A | A | L | G | K | M | V | G | V | S | N | V | A | I | S | Q | W | E | R |

Fig. 5A

| operator | double strand sequence |
|---|---|
| $O_1$ | A A C T A T C C A A T T T G T C A A G T T<br>T T G A T A G G T T A A A C A G T T C A A |
| $O_2$ | A A C T T T C C A A A T T G A C A A G T T<br>T T G A A A G G T T T A A C T G T T C A A |
| $O_3$ | A A C T A G C C A A T T T G T C A A G T T<br>T T G A T C G G T T A A A C A G T T C A A |

Fig. 5B

| operator site | sequence |
|---|---|
| $O_1$ | A A C T A T C C A A T<br>A A C T T G A C A A |
| $O_2$ | A A C T T T C C A A A<br>A A C T T G T C A A |
| $O_3$ | A A C T A G C C A A T<br>A A C T T G A C A A |
| consensus | A A C T T G C C A A T<br>       A T A      A<br>          T |

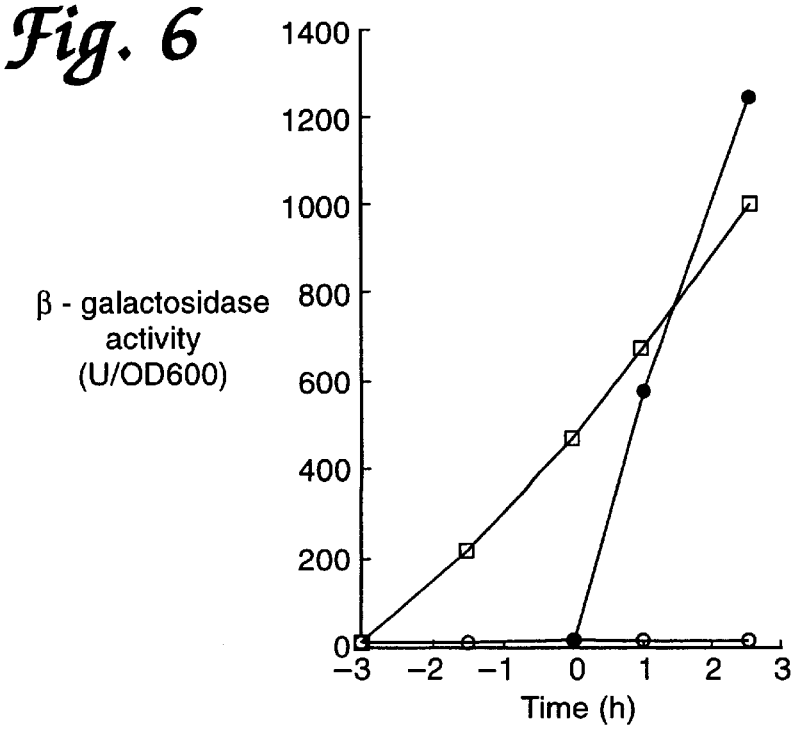

Fig. 6

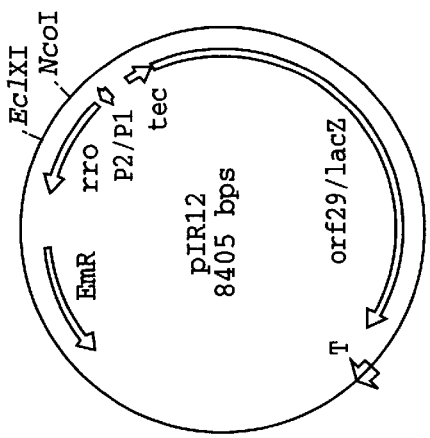

```
ATGAAAAAATACGTACCTGAAATGATTGATTATTTCAGAAGAGAATTGGACATGATGAAGATTGACGAGTCAGCTATTTCGAAATGGATAAAA          120
 M  K  K  I  R  L  P  E  M  I  D  Y  F  R  K  E  N  G  W  T  M  K  E  F  G  E  K  L  G  K  S  E  S  A  I  S  K  W  I  K        40
        NcoI
GGGGTTAGAGTCCCATGGTTGAAGATTTTGATAAATGGTCAATCTATTCGAGACCTAATCACTGATCCTGAGACATTAATGTATGGTGCTTCTGACCTTTCTACAACTCTATCCGAAATAAATAAA    240
 G  V  R  S  P  M  V  E  D  F  D  K  M  V  N  L  F  N  T  D  P  E  T  L  M  Y  G  A  S  D  L  S  T  T  L  S  E  I  N  K        80
ATCAGTTCAACTCGAAGAACCAGTCCAAAGTTGTTTAAAGAATCAGTTAGAATGAGCAAAACCAAGAAATCTAAAGGAATTCAATTAATAAAATA      360
 I  S  S  Q  L  E  E  P  R  Q  K  V  V  L  N  T  A  N  N  Q  L  D  E  Q  N  Q  E  K  K  K  E  S  K  V  I  P  I  N  K  I      120
CCTGACGATTTACCACCATATATAAGTAGAAAGATTTTAGAGAATTTCGTTATGCCTACAAACACTATGGAATATGAGGCTGATGAAGATATGGTCGATGTTCCTATTCTTGGTAGGATA        480
 P  D  D  L  P  P  Y  I  S  R  K  I  L  E  N  F  V  M  P  T  N  T  M  E  Y  E  A  D  E  D  M  V  D  V  P  I  L  G  R  I      160
        Ec1XI
GCCGGCCCGACTTCCTCCTTGATGCAGTAGAAAACTTCGACGGTACAAGACCAGTTCCAGCTCATTTCCTGTCGTGATTACTATTGGTTAATGGTTGATGGGCATAGCATGGAA         600
 A  A  G  L  P  L  D  A  V  E  N  F  D  G  T  R  P  V  P  A  H  F  L  S  S  A  R  D  Y  Y  W  L  M  V  D  G  H  S  M  E      200
CCGAAAATTCCATATGGAGCTTTATGTTTTAATTGAAGTTCTGATGTGAGCTACTATTGGAGCTGTTCATGCTCATGATGATTGCCAAGCAACATTAAAAAAAGTTTATCAT     720
 P  K  I  P  Y  G  A  Y  V  L  I  E  A  V  P  D  V  S  D  G  T  I  G  A  V  L  F  H  D  D  C  Q  A  T  L  K  K  V  Y  H      240
GAAATAGATTGCTTGAGACTTGTGTCAATCAACAAGAATTTAAAGACCAATTCTGTCAAGCTGTCAAGCTGTCAAAGTAGAAATTGATTTA       834
 E  I  D  C  L  R  L  V  S  I  N  K  E  F  K  D  Q  F  A  T  Q  D  N  P  A  A  V  I  G  Q  A  V  K  V  E  I  D  L              278
```

COMPLEX INDUCIBLE PROMOTER SYSTEM DERIVABLE FROM A PHAGE OF A LACTIC ACID BACTERIUM (LAB), AND ITS USE IN A LAB FOR PRODUCTION OF A DESIRED PROTEIN

This application is the national phase of international application PCT/NL95/00172, filed May 12, 1995 which designated the U.S.

BACKGROUND OF THE INVENTION

1. Field of the Invention

The present invention relates to a complex inducible promoter system derivable from a phage of a lactic acid bacterium.

2. Background of the Invention and Prior Art

Although complex inducible promoter systems are known in Gram-negative bacteria like *E. coli* and in the Gram-positive bacterium *Bacillus subtilis*, no such promoter system has been described for lactic acid bacteria or their phages.

The invention is directed to an inducible strong promoter for lactic acid bacteria, which preferably can be induced in a food-grade manner. Although various constitutive, weak and strong, promoters for lactic acid bacteria are known, there is still a need for an inducible promoter effective in lactic acid bacteria.

BRIEF SUMMARY OF THE INVENTION

The invention provides a complex inducible promoter system derivable-from a phage of a lactic acid bacterium, in particular a complex inducible promoter system comprising the DNA sequence given in FIG. 2 and SEQ. ID. NOS: 3–6 or a functionally equivalent DNA sequence. A suitable embodiment is formed by a DNA sequence essentially corresponding to the DNA sequence of sequence id no 3. Other alternative embodiments comprise at least an essential part of such a complex inducible promoter system such as the DNA sequence given in FIG. 3 (which is the part of FIG. 2 or sequence id. no. 3 lacking ORF 29 and its ribosome binding site RBS). The promoter system can be modified by replacing the mitomycin C induction system by a food-grade system, such as a temperature-initiated induction system or a salt-initiated induction system by mutation techniques known per se.

"A functional equivalent promoter system to that of sequence id no 3" is understood as to include variants and mutants that have a different nucleic acid sequence but form a functional inducible complex promoter which is capable of regulating expression of a gene operatively linked to it under inducing circumstances or after having undergone induction to a degree comparable to the specifically disclosed sequences forming a complex inducible promoter system according to the invention.

For example the nucleic acid sequences linking and flanking certain essential elements of the complex promoter system required for it to function as an inducible promoter can be different to those in the disclosed nucleic acid sequence id no 3. Preferably the length of such linking and flanking sequences will be the same as in the disclosed sequences in order to maintain a similar structure to that of the disclosed sequences of sequence id no 3. The spacing and orientation of the elements should be preferably be the same as of the nucleic acid sequences in sequence id no. 3. The essential elements are a combination of operator sequences 1 and 2, the repressor gene (ORF 27), the topological equivalent of cro gene (ORF 28) and the ribosomal binding sites of the corresponding genes, the SD sequence and the promoters of the genes.

A number of variations or mutations that can be considered to be obvious to a person skilled in the art in comparison to the illustrated nucleic acid sequences whilst still retaining the functionality of the complex inducible promoter and thus being considered functionally equivalent will now be presented. Any variations or mutations of the complex inducible promoter system encoded by the nucleic acid sequence not impairing the expression capacity of the promoter system or the foodgrade status is considered to fall within the scope of the invention. With regard to the expression products of ORF 27, ORF 28 and ORF 29 it is obvious that various nucleic acid sequences encode the same amino acid sequences of these expression products other than the nucleic acid sequence of sequence id no 3 or segments 880-1654, 390-350, 336-1 of Sequence id no 3. Simply by substituting one or more codons encoding the same amino acid a nucleic acid sequence different to that of Sequence id no 3 can be obtained which will be functionally equivalent to the complex inducible promoter system formed by Sequence id no 3. These functionally equivalent nucleic acid sequences naturally fall within the definition of functional equivalent and any nucleic acid sequence differing from the specifically illustrated nucleic acid sequences merely in this aspect fall within the scope of the invention.

Also the complex inducible promoter system will retain its functionality if mutations are incorporated in any of the aforementioned polypeptide encoding parts (ORF 27, ORF 28 or ORF 29), which do not affect the functionality of the resulting polypeptide. In general nucleic acid sequences encoding polypeptides can vary quite substantially without affecting the functionality of the expression product. Amino acid sequences with an overall homology of more than 50% are already considered to be likely to exhibit the same function. Using computer programmes it is quite simple to predict whether a particular sequence is sufficiently homologous to be a functional equivalent, so a person skilled in the art will be able to ascertain what modifications of these particular portions of the nucleic acid sequence forming the complex inducible promoter system will lead to expression products that are functionally equivalent to those encoded by ORF 27, 28 and 29 of Sequence id no 3 and thus also can form essential elements of a functionally equivalent promoter system, such a mutant promoter system thereby falling within the scope of the invention. Functionally equivalent elements of ORF 27, ORF 28 and ORF 29 are generally nucleic acid sequences having the same length as the respective ORF's of sequence id no 3 and exhibiting more than 50% homolgy, preferably more than 60%, more preferably more than 70% with most preference for 80–100% homology at amino acid level with the respective expression products of the respective ORF's.

Functionally equivalent elements of ORF 27, ORF 28 and ORF 29 are generally also nucleic acid sequences having the same length as the respective ORF's of sequence id no 3 and exhibiting hybridisation with the respective ORF's under normal to stringent hybridisation conditions. In general if a nucleic acid sequence can hybridize under normal to stringent conditions to an ORF 27, 28 or 29 and the expression product functions in an analogous manner to the non mutated expression product it can be used as a functional equivalent of that element in a complex inducible promoter system according to the invention.

Mutations of one to 5 amino acids mostly do not affect the functionality of the polypeptide expression product and thus nucleic acid sequences encoding a polypeptide differing from a polypeptide encoded by ORF 27, ORF 28 or ORF 29 merely by one to 5 amino acids can be considered as functionally equivalent elements of ORF 27, ORF 28 or ORF 29 for a complex inducible promoter system according to the invention. A complex inducible promoter system comprising one or more of such mutants as elements therefore falls within the scope of the invention.

Certainly now the bacteriophage repressor gene (ORF 29) and tec gene (ORF 28) have been sequenced a person skilled in the art will quite readily be able to either synthesize an equivalent sequence to replace the natural sequence illustrated in the ORFs 27, 28 and 29 or to search the genomes of other bacteriophages derivable from lactic acid bacteria for functionally equivalent sequences forming part of a natural complex inducible promoter system of a type according to the invention. This can be done by using the knowledge of nucleic acid sequences and/or amino acid sequences to screen known sequences for similar structures or to use probes or primers designed on the basis of the information now provided to screen genomic libraries for corresponding sequences and subsequently following the methodology of the subject invention to finally obtain the desired promoter system. DNA nucleotide and amino acid sequences obtained can be analyzed for example with the PC/GENE (version 6.7) sequence analysis program (IntelliGenetics, Inc., Geneva, Switzerland). Protein homology searches can be carried out with the data bases SWISSPROT (release 27) and the ATLAS of protein and genomic sequences (March, 1994) by means of the FASTA program (12). The technologies to be applied are well known to a person skilled in the art and can be carried out without requiring inventive skill, merely standard experimentation.

Apart from the computer programmes and the hybridisation tests it is also possible to carry out activity assays on the expression products to ascertain whether the function of the polypeptide is maintained. Thus a person skilled in the art can readily ascertain whether a particular nucleic acid sequence falls within the scope of being a functional equivalent of an element ORF 27, ORF 28 or ORF 29 or of a complex promoter system according to the invention using standard techniques. Naturally combinations of the above mentioned groups of variations and mutations can also be considered to fall within the scope of the invention.

Examples of complex inducible promoter systems falling within the scope of the invention are now illustrated.

A complex inducible promoter system derivable from a phage of a lactic acid bacterium, in particular comprising the DNA sequence of FIG. 2 or Sequence id no 3 or a functional equivalent thereof is claimed. A suitable embodiment of a functional equivalent complex inducible promoter system according to the invention as disclosed above comprises at least the following elements: a gene encoding a repressor equivalent to the repressor encoded by ORF 27, the corresponding RBS of ORF 27, the −35 and −10 promoter sequences of P2, operator sequence 01, operator sequence 02, the −35 and −10 promoter sequences of P1, a gene encoding a protein equivalent to tec encoded by ORF 28, the corresponding SD sequence of said gene, the RBS of ORF 29 and the nucleic acid sequence encoding an amino acid sequence equivalent to the amino acid sequence encoded by ORF 29, the elements being linked by intervening sequences and optionally flanked by flanking sequences, said intervening sequences and optionally said flanking sequences having the same length as in the sequence of FIG. 2 or Sequence id no 3 but not necessarily the same composition and the elements having the same order and direction of operation as in FIG. 2 or Sequence id. no 3. In particular an embodiment of the invention is formed by a complex inducible promoter system as disclosed above comprising at least the following elements: the nucleic acid sequence ORF 27, the corresponding RBS of ORF 27, the −35 and −10 promoter sequences of P2, operator sequence 01, operator sequence 02, the −35 and −10 promoter sequences of P1, the nucleic acid sequence ORF 28, the corresponding SD sequence of ORF 28, the RBS of ORF 29 and the nucleic acid sequence ORF 29, the elements being linked by intervening sequences and optionally flanked by flanking sequences, said intervening sequences and optionally said flanking sequences having the same length as in the sequence of FIG. 2 or Sequence id no 3 but not necessarily the same composition and the elements having the same order and direction of operation as in FIG. 2 or Sequence id. no 3. Preferably the flanking sequences and intervening sequences will be the same as in sequence id no 3 as this mimics the natural situation.

The presence of the sequence OBF 29 is optional. It has been found however that this sequence provides a suitable precursor sequence to the gene the complex inducible promoter system is to control. The length of this ORF 29 and the corresponding RBS are suitable for operatively linking the complex inducible promoter system to the gene to be controlled. A person skilled in the art will realize that variations of this region are possible without eliminating the inducible character or the ability of a complex promoter according to the invention to control expression of a gene placed 5' of ORF 28.

A suitable embodiment of the invention can thus also be formed by a complex inducible promoter system derivable from a phage of a lactic acid bacterium, which comprises the DNA sequence id no 3 (equal to the part of the DNA sequence given in FIG. 2 or Sequence id no 3 3' downstream from the codon encoding the terminal Ser of tec in ORF 28) or a functional equivalent thereof. Such a functional equivalent comprises the following elements: a gene encoding a repressor equivalent to the repressor encoded by ORF 27, the corresponding RBS of ORF 27, the −35 and −10 promoter sequences of P2, operator sequence 01, operator sequence 02, the −35 and −10 promoter sequences of P1, a gene encoding a protein equivalent to tec encoded by ORF 28, the corresponding SD sequence of said gene, the RBS of ORF 29 and the nucleic acid sequence encoding an amino acid sequence equivalent to the amino acid sequence encoded by ORF 29, the elements being linked by intervening sequences and optionally flanked by flanking sequences, said intervening sequences and optionally said flanking sequences having the same length as in the sequence of FIG. 2 or Sequence id no 3 but not necessarily the same composition and the elements having the same order and direction of operation as in FIG. 2 or Sequence id. no 3. In particular such a functional variant embodiment of the invention comprises at least the following elements: the nucleic acid sequence ORF 27, the corresponding RBS of ORF 27, the −35 and −10 promoter sequences of P2, operator sequence 01, operator sequence 02, the −35 and −10 promoter sequences of P1, the nucleic acid sequence ORF 28, the corresponding SD sequence of ORP 28, the RBS of ORF 29 and the nucleic acid sequence ORF 29, the elements being linked by intervening sequences and optionally flanked by flanking sequences, said intervening sequences and optionally said flanking sequences having the same length as in the sequence of FIG. 2 or Sequence id no 3 but not necessarily the same composition and the elements having the same order and direction of operation as in FIG. 2 or Sequence id. no 3. Preferably the flanking sequences and intervening sequences will be the same as in sequence id no 3 as this mimics the natural situation.

There is a possibility that operator sequence 03 of sequence id no 3 is not an essential element, however it is preferred that in a complex promoter system according to the invention the amino acid sequence and more preferably also the nucleic acid sequence of 03 is present as further essential element at the terminal part of ORF 28 or at the terminal part of the functional equivalent of ORF 28 as this will mimic the naturally operating promoter system more closely.

Hybrid sequences containing a complex inducible promoter system or essential part thereof according to the invention coupled to other homologous or heterologous DNA sequences including regulatory regions also fall within the scope of the invention.

As stated above the modification of such a complex promoter system also falls within the scope of the invention, the practical use of such a promoter system can be greatly improved by a modification of a complex inducible promoter system or an essential part thereof as disclosed above in various embodiments, such that under inducing circumstances or after being subjected to inducing circumstances the expression product of the repressor gene can no longer repress the promoter system, said inducing circumstances occurring via a food grade induction mechanism. Such a modification can arise for example when the gene encoding the repressor is mutated such that the expression product thereof is made incapable of repression via a food grade induction mechanism under inducing circumstances or after having been subjected to inducing circumstances. This can occur at the level of the operator binding sites or at the level of the repressor. A particular embodiment of a modification comprises a modification of a complex inducible promoter system of any of the above disclosed types which is located within the repressor gene. A suitable embodiment of a desirable modification comprises a modification of a complex inducible promoter system of any of the above disclosed types, wherein the modification renders the repressor incapable of binding to the complex promoter system via a food grade induction mechanism under inducing circumstances or after having been subjected to inducing circumstances. In particular a suitable modification of this type is one in which the food-grade system is a temperature-initiated induction system. We illustrate such a modified complex inducible promoter system, wherein the modification is located in the repressor gene as comprised on plasmid pIR14 and deposited as *Lactococcus lactis* subsp. *cremoris* LL302(pIR14) at Centraal Bureau voor Schimmelcultures in Baarn, The Netherlands in accordance with the Budapest Treaty on May 11, 1995 with accession number CBS 327.95. Such a modified inducible complex promoter is a foodgrade strong promoter suitable for expression of a desired gene in lactic acid bacterium.

The invention also provides a recombinant vector and a transformed lactic acid bacterium each comprising such complex inducible promoter system or an essential part thereof, which lactic acid bacterium is either the natural host of the phage from which the complex inducible promoter system is derivable, or a different lactic acid bacterium. In particular such a transformed lactic acid bacterium, obtainable through transformation with a recombinant vector according to the invention, said transformed lactic acid bacterium comprising a complex inducible promoter system or an essential part thereof as disclosed in any of the embodiments above free of the bacteriophage sequences normally associated with the promoter system when incorporated in it's native bacteriophage is covered by the scope of the invention. A recombinant vector or transformed lactic acid bacterium will preferably further comprise a desired gene that is to be expressed upon induction, said desired gene being operatively linked to a complex inducible promoter system according to the invention in any of the modified or non modified embodiments disclosed.

Further the invention provides a process for the production of a desired expression product like a protein by a transformed lactic acid bacterium, which comprises the expression of a gene encoding said desired protein or a precursor thereof under control of a complex inducible promoter system or an essential part thereof according to the invention. Preferably the transformed lactic acid bacterium is food-grade due to the presence of food-grade DNA sequences and/or absence of non-food-grade DNA sequences. For some embodiments it is desirable that the desired protein is secreted by the lactic acid bacterium due to the presence of a DNA sequence fused to the gene encoding the desired expression product and effecting secretion of the desired expression product, said expression product for example being a protein or a precursor thereof. For ease of production the sequences closest to that of a complex inducible promoter system in its natural setting will be used as this is preferred for quickly being able to commercially produce recombinant expression products that can be consumed by humans with the minimum of legislative problems.

A process in which the complex inducible promoter system can be used in a manner known per se for promoters is a fermentation process. In particular a fermentation process for producing a product for consumption or being applied to humans is a suitable process, most particularly when a food grade induction mechanism can be applied to regulate the expression of a product controlled by a complex inducible promoter according to the invention.

Very elegantly other inventions disclosed in two copending patent applications (EP-94201354.1 and EP94201353.3) filed on May 12, 1994 directed at processes of production using foodgrade organisms can be combined with the current invention. The processes and recombinant vectors disclosed in these applications can be applied in concert with the subject invention. For example the desired expression product to be expressed, i.e. the expression product encoded by the nucleic acid sequence operatively linked to the complex inducible promoter system of the subject invention can be a lysis protein and/or a holin causing lysis of the bacterial cells so that the contents of the cells can be released. The embodiments of vectors and processes can be considered to be incorporated by reference in the subject patent application in combination with the presence of a complex inducible promoter system according to the subject invention. Alternatively the desired expression product can be an enzyme involved in flavour formation, or in a fermentation process, in which the desired expression product is a protein having a function in a cheese production process, such as chymosin or a precursor thereof, or an enzyme involved in flavour formation.

The invention is illustrated below on the basis of a draft publication.

Inducible Gene Expression Mediated by a Repressor-operator System Isolated from *Lactococcus lactis* subsp. *cremoris* Bacteriophage R1-t

SUMMARY

A regulatory region of the temperate small isometric-headed *Lactococcus lactis* subsp. *cremoris* bacteriophage R1-t chromosome has been cloned and characterized. Sequence analysis revealed the presence of two divergently oriented Open Reading Frames (ORFs), each preceded by a sequence identical to the consensus promoter used by the vegetative form of RNA polymerase. The region contained three 21-bp direct repeats with internal dyad symmetry which could act as operators. Two of these repeats were separated by only 2 base pairs and partially overlapped the two potential promoter sequences. The third repeat was located at a distance of 380 bp from the other two at the end of one of the ORFs. To study possible transcriptional regulation of the region, a lacZ translational fusion with an ORF following one of the identified ORFs was constructed. Under conditions that favour the lysogenic life cycle of R1-t, β-galactosidase activity was very low. However, the expression of the lacZ fusion could be induced by the addition of mitomycin C, which promotes the switch to the lytic life cycle. This resulted in a 70-fold increase in the production of β-galactosidase as compared to the non-induced situation. In non-induced cells promoter activity was assumed to be repressed by the rro gene product, because a frameshift mutation in the rro gene resulted in constitutive expression of the lacZ gene fusion.

INTRODUCTION

Gram-positive lactic acid bacteria (LAB) are used in a variety of industrial food and dairy fermentations as part of a starter culture, inoculated in order to drive the primary fermentation. A major problem is bacteriophage contamination of the culture which can result in the failure of the fermentation process (10). A better understanding of the bacteriophage life cycle would possibly allow the development of strategies to prevent phage infections. In addition, the study of lysogeny could offer powerful tools for the design of regulatory gene expression systems.

Until recently characterization of lactococcal bacteriophages was mainly limited to phage morphology, protein composition, and DNA homology-determinations, on the basis of which the bacteriophages have been grouped into different classes (9). Although many reports on lysogeny among Lactococci have been published, little is known about the molecular basis for control and maintenance of the lysogenic relationship in LAB hosts. A putative regulator gene, bpi (for BK5-T promoter inhibitor), of the temperate *L. lactis* subsp. *cremoris* phage BK5-T has been cloned (11). The bpi gene product inhibited the activity of some identified BK5-T promoters. The mechanism by which the bpi gene product operates is unknown.

In the context of the ultimate aim to develop a gene expression system, which can be turned on by temperature, we report here the characterization of a regulatory region of the chromosome of the temperate small isometric-headed *Lactococcus lactis* subsp. *cremoris* bacteriophage R1-t. The data presented show that a specific DNA fragment of bacteriophage R1-t contains an ORF (rro) that specifies a protein capable of repressing gene expression, presumably from an overlapping promotor-operator region ($P_1$) encompassed by the same fragment. With the use of a lacZ reporter gene, it is shown that this regulatory region can be exploited for the construction of inducible gene expression systems in *L. lactis*.

BRIEF DESCRIPTION OF THE DRAWINGS

FIG. 1B shows the nucleic acid sequence (SEQ ID NO: 1) and corresponding deduced amino acid sequence (SEQ ID NO: 2) at the fusion site between ORF 29 and the lacZ gene in plasmid pIR12.

FIG. 2 (comprising FIGS. 2A, 2B and 2C) depict the double strand nucleotide sequence of the 1888 bp HindIII$^{(1)}$/Pvu$^{(2)}$ fragment (SEQ ID NO: 3). The −10 and −35 sequences of the two divergent putative promoters, $P_1$ and $P_2$, are underlined. The 21-bp direct repeats with dyad symmetry $O_1$, $O_2$ and $O_3$ are shaded. The deduced amino acid sequences of the ORFs are indicated and relevant restriction enzyme sites are in bold-face type. Stop codons are indicated by asterisks. The putative ribosomal binding sites (RBS) of ORF 27 and ORF 28 are indicated in italic, and the putative alpha-helix-turn-alpha helix in the deduced amino acid sequences of ORF 27 and ORF 28 are doubly underlined.

FIG. 3 shows the alignment of the deduced amino acid sequence of ORF 27 (SEQ ID NO: 6), *Bacillus subtilus* DinR protein (SEQ ID NO.: 8) and the cI repressor of the *E. coli* bacteriophage 434 (SEQ ID NO: 7). Identical amino acid residues are indicated by asterisks and conservative changes are indicated by dots.

FIG. 4 shows an alignment of the putative helix-turn-helix motifs in rro and tec with the transcriptional control proteins of three *E. coli* bacteriophages (λ.CII, SEQ ID NO: 10; φ80 gp30, SEQ ID NO: 9; and P22 C2, SEQ ID NO 11). The sequences were taken from Dodd et al. (4). Segments of the ORF 27 (SEQ ID NO: 6) and ORF 28 (SEQ ID NO: 5) sequences having a strong likelihood for adopting the same helix-turn-helix conformation are shown, and strongly conserved amino acids in the motif (Ala or Gly in position 5, Gly in position 9, and Ile or Val in position 15) are underlined.

FIGS. 5A and 5B show the putative operator sites contained within the 1888-bp HindII/PvuII fragment (SEQ ID NO: 3). The double strand sequences of the putative operator sites $O_1$, $O_2$ and $O_3$ are shown in FIG. 5A. The central base pair, the axis of symmetry, is shown in bold-face type. Alignment of the six half-sites enabled the designation of an 11 base pair long consensus half-site, shown in FIG. 5B.

FIG. 6 shows the effect of mitomycin C on β-galactosidase activity in *L. lactics* subsp. *cremoris* strain LL302 cells carrying plasmid pIR12 (dark circles) as a function of time. The time point at which 1 μg/ml mitomycin C was added is denoted by $t_0$. The β-galactosidase activities measured in cells carrying pIR12 and pIR13 in the absence of mitomycin C are represented by open circles and open squares, respectively. Time scale is in hours before and after $t_0$.

FIG. 7 shows the restriction enzyme sites NcoI and EclXI for primers rro1 and rro2 in plasmid pIR12.

FIG. 8 is the nucleic acid and corresponding deduced amino acid sequence of rro sequence (bases 820-1654 of SEQ ID NO: 3). The NcoI and EclXL restriction enzyme sites within rro are indicated in bold.

DETAILED DESCRIPTION OF THE INVENTION

Materials and Methods

Bacterial Strains, Phage, Plasmids, and Media

Figure 1A:
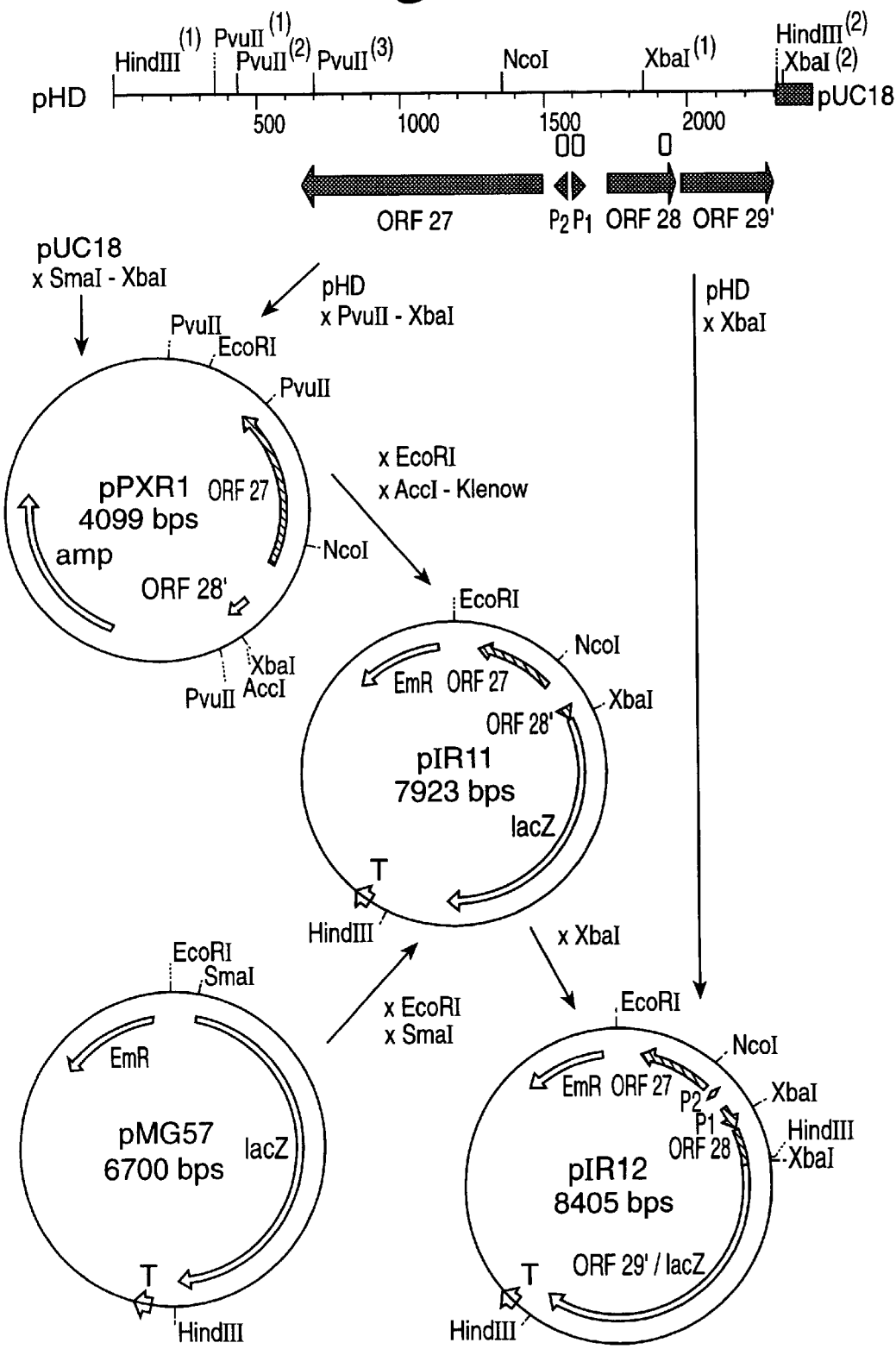
FIG. 1A depicts the 1428 bp PVUII$^{(2)}$/XbaI$^{(1)}$ fragment of pHD subcloned into pUC18 restricted with SmaI and XbaI, resulting in plasmid pPXR1. The production of pIR12 from pPXR1, in which ORF 29 was fused in frame to the lacz gene of *E. coli* by cloning the 482-bp XbaI fragment of pHD into the unique XbaI site of pIR11, is presented as a flow chart. The three 21 bp direct repeats are symbolized by open boxes. The ORFs that were subcloned are shaded. EM$^R$ (erythromycin resistance marker), Amp$^R$ (ampicillin resistance marker) and T (transcription terminator) are shown were indicated.

The bacterial strains, phage and plasmids used in this study are listed in Table 1. *Escherichia coli* was grown in TY broth (22) or on TY broth solidified with 1.5% agar. *L. lactis* was grown in glucose M17 broth (25), or on glucose M17 agar. Erythromycin was used at 100 µg/ml and 5 µg/ml for *E. coli* and *L. lactis*, respectively. The chromogenic substrate 5-bromo-4-chloro-3-indolyl β-D-galactopyranoside (X-gal) (Sigma Chemical Co., St.Louis, Mo.) was added to plates at a final concentration of 40 µg/ml.

DNA Techniques

Plasmid DNA was isolated essentially by the method of Birnboim and Doly (1). Restriction enzymes, Klenow enzyme, and T4 DNA ligase were obtained from Boehringer GmbH (Mannheim, Germany) and used according to the instructions of the supplier. All plasmids were constructed in *E. coli*, which was transformed by the method of Mandel and Higa (15). Plasmids were introduced in *L. lactis* subsp. *cremoris* LL302 by means of electroporation (31). DNA and protein sequences were analysed using the programs developed by Staden (24). Helix-turn-helix motif predictions were performed according to Brennan (2)

β-galactosidase activity per OD600 was determined essentially as described by Miller (16).

Plasmid Constructions

A 2.2-kb R1-t HindIII fragment containing a putative genetic switch involved in control of lysogeny of bacteriophage R1-t (32), was subcloned in the unique HindIII site of pUC18 resulting in the plasmid pHD. The 1428-bp PvuII[(2)]/XbaI[(1)] fragment of pHD was subcloned into pUC18 restricted with SmaI and XbaI (FIG. 1A). The resulting plasmid, pPXR1, was restricted with AccI and the 5'-protruding ends were flushed with Klenow enzyme. The linearized vector was subsequently digested with EcoRI and the fragment carrying ORF 27 and the partial ORF 28 was ligated into EcoRI-SmaI-digested pMG57, resulting in plasmid pIR11. To restore ORF 28 and to fuse ORF 29 in frame to the lacZ gene of *E. coli*, the 482-bp XbaI fragment of pHD was cloned into the unique XbaI site of pIR11 resulting in plasmid pIR12. The amino acid sequence at the fusion site between ORF 29 and the lacZ gene is shown in FIG. 1B.

TABLE 1

Bacterial strains, plasmids and bacteriophage.

| | relevant features | reference |
|---|---|---|
| *Bacterial strains* | | |
| *L. lactis* subsp. *cremoris* | | |
| LL302 | MG1363 carrying the pWV01 repA gene on the chromosome | CBS 327.95 |
| *E. coli* | | |
| MC1000 | araD139, Δlacx74, Δ(ara, leu)7697, galU, galK, strA | 3 |
| *Plasmids* | | |
| pUC18 | Ap$^R$ | 33 |
| pHD | Ap$^R$; pUC18 derivative, containing a 2.2-kb HindIII-fragment of phage R1-t | This work |
| pPXR1 | Ap$^R$; carrying a 1428-bp PvuII/XbaI fragment of pHD | This work |
| pMG57 | Em$^R$; lacZ fusion vector, replicates in *E. coli* and *L. lactis* | 29 |
| pIR11 | Em$^R$; pMG57 derivative, carrying a 1450-bp EcoRI/AccI fragment of pPXR1 | This work |
| pIR12 | Em$^R$; pIR11 derivative, carrying a 482-bp XbaI fragment of pHD | This work |
| pIR13 | Em$^R$; pIR12 derivative, carrying a frameshift mutation in rro | This work |
| *Bacteriophage* | | |
| R1-t | type P335, small isometric lactococcal phage, isolated from *L. lactis* subsp. *cremoris* R1 | 9.14 |

Em$^R$, Ap$^R$ represent resistances to erythromycin and ampicillin, respectively.

Mitomycin C Induction

Overnight cultures were diluted hundred-fold in fresh glucose M17 medium and grown until the culture reached an OD600 of 0.3 at which point mitomycin C (Sigma) was added to a final concentration of 1 µg/ml.

Assay of β-galactosidase Activity

Cells from 5 ml of cultures were collected by centrifugation and resuspended in 1 ml of cold Z-buffer (16). Glass beads (0.1 mm in diameter) were added and the cells were disrupted at 4° C. for 15 minutes using a "Shake it, Baby" cell disrupter (Biospec Products, Bartleville, Okla.). Cells debris was removed by centrifugation for 5 min in an Eppendorf centrifuge. Equal amounts of supernatant (0.5 ml) and cold Z-buffer were mixed and specific pIR13 was constructed as follows. To introduce a frameshift mutation in ORF 27 pIR12 was restricted with NcoI and the resulting 5'-sticky ends were filled in with Klenow enzyme. After selfligation an NsiI restriction site was created in the resulting plasmid pIR13, as was verified by digestion with this enzyme, thus confirming that a frameshift mutation had been introduced in ORF 27.

RESULTS

Analysis of the Nucleotide Sequence of the Bacteriophage R1-t Regulatory Region

We recently determined the complete nucleotide sequence of the temperate *L. lactis* subsp. *cremoris* bacteriophage R1-t (32). All of the identified ORFs had the same orientation, except for a cluster of three consecutive ORFs, the first of which is ORF 27, that had an orientation opposite to that of the two other ORFs (28 and 29). The non-coding region between the oppositely directed ORF 27 and ORF 28 contained two divergently oriented sequences identical to the consensus promoter sequence used by the vegetative form of RNA polymerase of *L. lactis* (30). FIG. 2 represents the nucleotide sequence of the 18889-bp HindIII$^{(2)}$/PvuII$^{(2)}$ fragment, containing the two divergent putative promoters (designated $P_1$ and $P_2$) and the ORFs on this DNA fragment, which will be discussed below (see SEQ. ID. NO: 3).

The deduced amino acid sequence of ORF 27 (see SEQ. ID. NO: 6) shows significant similarity with the *Bacillus subtilis* DinR protein, the repressor of a set of damage inducible genes, corresponding to the LexA repressor of *E. coli* (21) and the c1 repressor of the *E. coli* bacteriophage 434 (17). These similarities are shown in FIG. 3 and suggest that ORF 27, designated hereafter as rro, might specify the bacteriophage R1-t repressor protein (see SEQ. ID. NOS: 6, 8 and 7). A putative ribosomal binding site could be identified upstream of rro with a ΔG of −11.8 kcal/mole according to Tinoco et al. (26). If the methionine immediately downstream of the putative ribosomal binding site would serve as the translational start of rro, the gene product would consist of 258 amino acids with an estimated molecular weight of 28,940 Da.

Since most bacteriophage-specific repressor proteins contain a so-called α-helix-turn-α-helix motif involved in binding of the protein to its DNA target, we compared the deduced amino acid sequence of rro with a "master set" of pre-aligned sequences taken from proteins known to contain a helix-turn-helix motif (2). The results of the alignment are shown in FIG. 4. By using an amino acid versus position score matrix (weight matrix) derived from amino acid conservations in the master set, an AAC (average amino acid change per codon)-score of 0.75 was obtained for a stretch of 20-amino acids, suggesting that this sequence is a strong candidate for adopting a helix-turn-helix conformation involved in binding to a specific DNA target (see SEQ. ID. NO: 6, 5, 10, 9 and 11). ORF 28 can specify a protein of 80 amino acids with a calculated molecular mass of 9,081 Da. Upstream of ORF 28 a potential ribosome binding site is present showing strong complementarity to the *L. lactis* 3' 16S rRNA sequence (ΔG=−19.4 kcal/mole) and a window of 8 bp. In addition to the topological similarity with the lambda cro gene, the ORF 28 amino acid sequence contains a stretch of amino acids with the characteristics of a putative helix-turn-helix motif (FIG. 4). ORF 28 therefore is designated hereafter as tec (topological equivalent of cro).

The intergenic region between rro and tec contains two almost perfectly matching 21-bp direct repeats with internal dyad symmetry, $O_1$ and $O_2$ (FIG. 2). They are separated by two nucleotides, overlap the −35 sequences of the two putative promoters in this region, and may function as operator binding sites for the R1-t repressor. Careful inspection of the entire 1889-bp HindIII/PvuII fragment revealed a third putative operator site, $O_3$, situated within the coding region of ORF 28 at a distance of 380 basepairs upstream of $O_1$. The double strand sequences of the putative operator sites are shown in FIG. 5A. Alignment of the six half-sites enabled the designation of an 11 base pair long consensus half-site (FIG. 5B), see FIG. 2.

The Expression of ORF 29 is Subject to Repression by the rro Gene Product

Analogous to the situation in the regulatory regions of several other temperate bacteriophages, the non-coding area between the divergently oriented ORFs could function as the regulatory region involved in lysogeny of the phage. In this scheme $P_1$ might function as the transcriptional start signal for the lytic genes, whereas $P_2$ might be responsible for the establishment of the lysogenic state.

To examine whether transcription of ORF 29 was regulated by upstream sequences, a lacZ-ORF 29 translational fusion was constructed in plasmid pIR12 (FIG. 1). In *L. lactis* subsp. *cremoris* LL302 cells carrying pIR12 very little β-galactosidase activity (17 U) was observed (FIG. 6). To determine whether lacZ expression could be induced under conditions which induce the lytic state, the effect of mitomycin C on β-galactosidase activity was examined. After the addition of 1 μg/ml of mitomycin C to a culture carrying pIR12, the β-galactosidase activity increased considerably. Two and a half hours after the addition of mitomycin C β-galactosidase activity had increased approximately 70-fold, indicating that ORF 29 was transcriptionally regulated, presumably by promoter $P_1$, because the region between ORF 28 and ORF 29 does not provide space for a promoter and because no promoter-like sequence could be discerned in the 3' region of ORF 28.

In order to examine whether the low lacZ expression in non-induced cells carrying plasmid pIR12 was established through repression of promoter activity by the rro gene product, pIR13 was constructed. Filling-in the NcoI restriction site of pIR12 resulted in a frameshift mutation and the introduction of two stop codons in the rro gene. Cells containing pIR13 are not expected to produce a functional rro gene product. As can be seen from FIG. 6, such cells constitutively expressed lacZ at a high level. From these results we infer that the rro gene is required for the repression of ORF 29 transcription under conditions that favour the lysogenic state of the bacteriophage R1-t. Apparently inactivation of the rro gene by the introduction of a frameshift led to derepression of promoter activity required for ORF 29 transcription.

DISCUSSION

We recently determined the complete nucleotide sequence of the temperate *L. lactis* subsp. *cremoris* bacteriophage R1-t. All identified ORFs were oriented in one direction, except for a cluster of three consecutive ORFs, the first of which is ORF 27. The non-coding region between the oppositely directed ORF 27 and ORF 28 contains two divergently oriented sequences, designated $P_1$ and $P_2$, identical to the consensus promoter sequence used by the vegetative form of RNA polymerase of *L. lactis* (30). On the basis of significant similarity of the deduced amino acid sequence with various repressor proteins we assumed that ORF 27, designated rro, specifies the bacteriophage R1-t repressor protein. The deduced rro gene product is a protein of 258 amino acids with an estimated molecular weight of 28,940 Da.

To study possible transcriptional regulation of the region by the rro gene product, a lacZ translational fusion with ORF 29, which is located downstream of ORF 28, was constructed. It was shown that under conditions that favour the lysogenic life cycle of R1-t, β-galactosidase activity was very low. Expression of the lacZ fusion could be induced by the addition of mitomycin C, which promotes the switch to the lytic life cycle. In non-induced cells promoter activity is likely to be repressed by the rro gene product, because a frameshift mutation in the rro gene resulted in constitutive expression of the LacZ gene fusion. These results indicate that ORF 29 is transcriptionally regulated, presumably by promoter $P_1$. It is likely that, analogous to several lambdoid phages, prophage induction is the result of cleavage of the phage repressor via a RecA-mediated pathway. DNA damage activates RecA, which presumably catalyzes self-cleavage of Rro at a site that seems to be conserved in proteins that undergo RecA-mediated cleavage (13).

The rro gene is directly preceded by the P2 promoter. The identity of the putative −10 and −35 sequences of P2 to the vegetative *L. lactis* promoter sequences is therefore consistant with the idea that the lysogenic response to infection by a temperate phage requires the synthesis of a phage-encoded repressor (20). The repressor gene therefore is probably one of the first phage genes to be expressed after infection and, consequently, its expression should rely entirely upon phage-specific transcription initiation sequences recognized by the host RNA-polymerase. A putative DNA-binding motif is present in the deduced Rro amino acid sequence. Like most of the bacteriophage-specified repressor proteins, Rro contains a so-called α-helix-turn-α-helix motif, suggesting that this stretch of amino acids is involved in binding to a specific DNA target, the so-called operator (19). The intergenic region between rro and tec contains two almost perfectly matching 21-bp direct repeats with internal dyad symmetry, designated $O_1$ and $O_2$. These sequences are separated by two nucleotides, overlap both −35 sequences of the two putative promoters in this region, and may function as operator binding sites for the R1-t repressor. Careful inspection of the entire 1889-bp HindIII/PvuII fragment revealed a third putative operator site, $O_3$, situated within the coding region of ORF 28 at a distance of 380 basepairs upstream of $O_1$. Of the 11 bp that constitute the operator half-site, 7 bp are invariable.

Most of the operators described hitherto consist of imperfect symmetrical binding sites. In the case of phage lambda operators, on which detailed structural information concerning protein-DNA complex formation is available, this 2-fold rotational symmetry reflects the two binding sites for each of the two subunits of the repressor dimer (18). The subtle structural variation in the individual binding sites of the operators form the basis for their differential relative affinities towards the c1 and cro products (20). With respect to the localization of the putative operators, however, there is an obvious difference in the organization of the R1-t immunity region compared to that of the studied *E. coli* phages. In contrast to the situation in lambda where the three operators are clustered in the non-coding area between the two divergent promoters, enabling co-operative binding, the third operator site ($O_3$) of R1-t is located 380 bp upstream of $O_1$, within the ORF 28 coding region. Such organization is not unique, since similar arrangements of multiple operator sites have been demonstrated in several *E. coli* operons, such as gal (7, 8), araBAD (5), deo (27) and Lac (6). In all these cases there is now accumulating evidence for a regulatory mechanism that involves cooperative binding of the repressor to the separated sites through protein-protein contacts holding together a loop of intervening DNA (23).

A similar situation has also been demonstrated for the *B.subtilis* phage φ105 (28). The third operator of φ105, designated $O_R3$, is located approximately 250 bp downstream from $P_R$, within the ORF 3 coding region of the proximal gene of the $P_R$ transcription unit. Although the three φ105 $O_R$ sites are required for maximal gene control during phage development, it was shown that repression of $P_R$ could be observed in the absence of the $O_R3$ copy. Preliminary results indicated that deletion of the $O_3$-containing 482-bp XbaI-fragment of pIR12, resulting in an in frame fusion of ORF 28 to the lacZ gene, had only a minor effect on the repression of expression of the fusion protein, suggesting that a similar situation exists in the case of R1-t. However, since the deletion of the XbaI-fragment also results in the inactivation of tec, further experiments have to reveal the exact role of $O_3$ in the control of lysogeny.

On the basis of the results obtained, it would appear that the general strategy employed by R1-t to control lysogeny is similar to that used by the lambdoid phages of *E. coli*. In this concept $P_1$ functions as the transcriptional start signal of the lytic genes and P2 is the equivalent initiator for the genes expressed during the lysogenic state, including rro which specifies the phage repressor. Although ORF 28, designated tec, is the topological equivalent of the lambda cro gene and the deduced amino acid sequence contains a putative DNA-binding α-helix-turn-α-helix motif, it has to be clarified whether the tec gene product is actually playing a role in the control of lysogeny and if so, whether it is the functional equivalent of cro.

Inducible gene expression in *E. coli* based on the temperature-sensitive C1 repressor C1857, has been extremely helpful as a simple means to overexpress (heterologous) genes in this organism. By analogy, to dispose of such a system in Lactococci would be valuable to modulate gene expression. Experiments were carried out to develop such a thermo-inducible gene expression system.

Construction of a Thermo-inducible Gene Expression System for *Lactococcus lactis*

Inducible gene expression in *Escherichia coli* based on the temperature-sensitive CI repressor CI857, has been extremely helpful as a simple means to overexpress (heterologous) genes in this organism. By analogy, to dispose of such a system in Lactococci would be valuable to modulate gene expression. We developed such a thermoinducible gene expression system for *Lactococcus lactis* on the basis of the regulatory region of the lactococcal temperate bacteriophage R1-t.

A regulatory region of the lactococcal temperate bacteriophage R1-t encompassing rro, encoding the phage repressor, and tec (the topological equivalent of phage lambda cro) was subcloned in such a way that the ORF immediately downstream of tec was translationally fused with lacZ in plasmid pIR12[34] (Nauta et al., 1994). Expression of the fused lacZ could be induced by the addition of 1 μg/ml mitomycin C to pIR12 containing cells.

In order to construct a thermo-inducible gene expression system, part of the rro gene (corresponding to the segment of Rro in which a mutation could result in a heat-labile repressor mutant[33], M. Lieb, 1991), was mutagenized using PCR and dITP[35] (J. J. Spee et al., 1993). The two synthetic primers used for amplification (Table 1) both encompassed a restriction enzyme site that was located within rro and unique in pIR12: NcoI and EclXI for primers rro1 and rro2 respectively (FIG. 7). After restriction of the PCR products with both enzymes, the NcoI/EclXI fragment of pIR12 could therefore be replaced by the mutagenized fragment.

Mutagenesis of rro

Random mutagenization of rro was performed by PCR essentially as described by Spee et al. (1993). A 372-basepair rro fragment was amplified with Supertaq polymerase (HT Biotechnology, Cambridge, England). The following conditions were used. Approximately 10 ng of pIR12 DNA was used as a template for PCR in a total volume of 50 μl, containing 1 unit of Supertaq polymerase, 10 mM Tris-HCl$_2$ pH 9.0, 5 mM MgCl$_2$, 50 mM KCl, 0.01% (w/v) gelatin, 0.1% Triton X-100, and 200 µM dNTP's. PCR reactions were performed in the presence of 200 µM dITP using 10 pmol of the primers rro1 and rro2 (Table 1). The concentration of the limiting dNTP was 14 µM. PCR fragments were purified by fenol/chloroform extraction, digested with NcoI and EclXI and subcloned in NcoI/EclXI digested pIR12. The ligation mixture was used to transform *Lactococcus lactis* LL302.

Screening for Temperature-sensitive Rro Mutants

Screening for mutations in Rro that resulted in a loss of DNA-binding activity at elevated temperatures was performed by using a plate assay. After transformation, cells were plated on GSM17 agar plates supplemented with 5-bromo-4-chloro-3-indolyl-β-D-galactopyranoside (X-gal) and incubated overnight at 30° C. By this procedure, the strain *Lactococcus lactis* subsp. *cremoris* LL302 (pIR14) was obtained. Colonies of this strain are white at 30° C. and blue at 37° C. The β-galactosidase activities at both temperatures were measured. The strain was grown to an OD600 of 0.3 at 30° C. after which time point the culture was divided in two parts. One half of the culture was grown at 30° C., the other part at 37° C. AFter two hours, the β-galactosidase activity of both cultures was determined. The β-galactosidase activity at 30° C. was slightly higher than that observed in the *Lactococcus lactis* subsp. *cremoris* LL302 strain carrying pIR12 (wild type Rro) due to some lacZ expression at this temperature (this leakage could be diminished by growing cells at lower temperatures). The lacZ expression in strain *lactococcus lactis* subsp. *cremoris* LL302 (pIR14) could be induced by a shift in temperature. In cells that were grown at 37° C., the lacZ expression had increased considerably. The mutation within rro is present on plasmid pIR14 deposited at CBS Baarn under accession nr. CBS 327.195.

REFERENCES

1 Birnboim, H. C., and J. Doly. (1979). A rapid alkaline extraction procedure for screening recombinant plasmid DNA. Nucleic Acids Res. 7: 1513–1523.
2 Brennan, R. G., and B. W. Matthews. (1989). The helix-turn-helix DNA binding motif. J. Biol. Chem. 264: 1903–1906.
3 Casadaban, M. J., and S. N. Cohen. (1980). Analysis of gene control signals by DNA fusion and cloning in *Escherichia coli*. J. Mol. Biol. 138: 179–207.
4 Dodd, I. B., and J. B. Egan. (1990). Improved detection of helix-turn-helix DNA-binding motifs in protein sequences. Nucleic Acids Res. 18: 5019–5026.
5 Dunn, T. M., Hahn, S., Ogden, S. and Schleif, R. F. (1984). An operator at -280 base pairs that is required for repression of araBAD operon promoter: Addition of DNA helical turns between the operator and promoter cyclically hinders expression. Proc. Natl. Sci. USA 81: 5017–5020.
6 Eismann, E., von Wilcken-Bergmann, B., and Müller-Hill, B. (1987). Specific destruction of the second Lac operator decreases repression of the lac operon in *Escherichia coli* fivefold. J. Mol. Biol. 195: 949–952.
7 Fritz, H. J., Bicknase, H., Gleumes, B., Heibach, C., Rosahl, S., and Ehring, R. (1983). EMBO J. 2: 2129–2135.
8 Irani, M. H., Orosz, L., and Adhya, S. (1983). A control element within a structural gene: the gal operon of *Escherichia coli*. Cell 32: 783–788.
9 Jarvis et al. (1991). Species and type phages of lactococcal bacteriophages. Intervirology 32: 2–9.
10 Klaenhammer, T. R. (1989). Genetic characterization of multiple mechanisms of phage defense from a prototype phage-insensitive strain, *Lactococcus lactis* ME2. J. Dairy Sci. 72: 3429–3445.
11 Lakshmidevi, G., Davidson, B. E., and Hillier, A. J. (1990). Molecular characterization of promoters of the *Lactococcus lactis* subsp. *cremoris* temperate bacteriophage BK5-T and identification of a phage gene implicated in the regulation of promoter activity. Appl. Environ. Microbiol. 56: 934–942.
12 Pearson W. R. and D. J. Lipman 1988. Improved tools for biological sequence comparison Proc. Natl. Sci USA 85:2444–2448.
13 Little, J. W. (1993). LexA cleavage and other self-processing reactions. J. Bacteriol. 175: 4943–4950.
14 Lowrie, R. J. (1974). Lysogenic Strains of Group N Lactic Streptococci. Applied Microbiology. 27: 210–217.
15 Mandel, M., and A. Higa. (1970). Calcium-dependent bacteriophage DNA infection. J. Mol. Biol. 53: 159–162.
16 Miller, J. (1972). Experiments in molecular genetics. Cold Spring Harbor Laboratory Press, Cold Spring Harbor, N.Y.
17 Nikolnikov, S., Posfai, G., and Sain, B. (1984). The construction of a versatile plasmid vector that allows direct selection of fragments cloned into six unique sites of the c1 gene of coliphage 434. Gene 30: 261–265.
18 Pabo, C. O., and Lewis, M. (1982). The operator-binding domain of lambda repressor: structure and DNA recognition. Nature (London) 298: 443–447.
19 Pabo, C. O., and Sauer, R. T. (1992). Transcription factors: structural families and principles of DNA recognition. Annu. Rev. Biochem. 61: 1053–1095.
20 Ptashne, M. (1986). A genetic switch, Cell and Blackwell Scientific Press, Cambridge, Mass.
21 Raymond-Denise, A., and Guillen, N. (1991). Identification of dinR, a DNA damage-inducable regulator gene of *Bacillus subtilis*. J. Bacteriol. 173: 7084–7091.
22 Rottlander, E., and T. A. Trautner. (1970). Genetic and transfection studies with Bacillus subtilis phage SP50. J. Mol. Biol. 108: 47–60.
23 Schleif, R. F. (1992). DNA looping. Annu. Rev. Biochem. 61: 199–223.
24 Staden, R. (1982). Automation of the computer handling of gel reading data produced by the shotgun method of DNA sequencing. Nucleic Acids Res. 10: 4731–4751.
25 Terzaghi, B. E., and W. E. Sandine. (1975). Improved medium for lactic streptococci and their bacteriophages. Appl. Microbiol. 29: 807–813.
26 Tinoco, I., Jr., Bore, P. N., Dengler, B., Levine, M. D., Uhlenbeck, O. C., Crothers, D. M., and Gralla, J. (1973). Improved estimation of secundary structure in ribonucleic acids. Nature 246: 40–41.
27 Vallentin-Hansen, P., Albrechtsen, B., and Love Larsen, J. E. (1986). DNA-protein recognition: demonstration of three genetically separated operator elements that are required for repression of the *Escherichia coli* deoCABD promoters by the DeoR repressor. EMBO. J. 5: 2015–2021
28 Van Kaer, L., Van Montagu, M., Dhease, P. (1987). Transcriptional control in the EcoR1-F immunity region of *Bacillus subtilis* phage φ105. Identification and unusual structure of the operator. J. Mol. Biol. 197: 55–67.
29 Van der Guchte, M., Kok, J., Venema, G. (1991) Distance-dependent translational coupling and interference in *Lactococcus lactis*. Mol.Gen.Genet. 227: 65–71.

30 Van der Guchte, M., Kok, J., Venema, G. (1992). Gene expression in *Lactococcus lactis*. FEMS Microbiol. Rev. 88: 73–92.

31 Van der Lelie, D., J. M. B. M. van der Vossen, and G. Venema. (1988). Effect of plasmid incompatibility on DNA transfer to *Streptococcus cremoris*. Appl. Environ. Microbiol. 54: 865–871.

32 Yanisch-Perron, C., J. Vieira, and J. Messing. (1985). Improved M13 phage cloning vectors and host strains: nucleotide sequences of the M13mp18 and pUC19 vectors. Gene 33: 103–119.

33 Lieb, M. 1981. A fine structure map of spontaneous and induced mutations in the lambda repressor gene, including insertions of IS elements. *Mol Gen Genet* 184: 364–371.

34 Nauta, A., A. M. Ledeboer, G. Venema, and J. Kok. 1994. Complex inducible promoter system derivable from a phage of a lactic acid bacterium and its use in a LAB for production of a desired protein. European Patent application nr. EP-PA-94201355.8

35 Spee, J. H., W. M. de Vos, and O. Kuipers. 1993. Efficient random mutagenesis method with adjustable mutation frequency by use of PCR and dITP. *Nucleic Acids Res* 21:777–778.

TABLE 2

Primers used to amplify part of *rro*

| Primer | 5'-3' nucleotide sequence | basepair position within *rro* (FIG. 2) |
|---|---|---|
| rro1 | GAA GTC CCA TGG TTG AAG ATT TTG | 128–151 |
| rro2 | CAA GAG GAA GTC CGG CCG CTA TCC | 476–499 |

* The *Nco*I and *Ecl*XI restriction enzyme sites are underlined

What is claimed is:

1. A complex inducible promoter system from a phage of a lactic acid bacterium, said complex inducible promoter system comprising a repressor protein alpha-helix-turn-alpha-helix region encoding sequence and an operator sequence with internal dyad symmetry, said complex inducible promoter system comprising the following elements in the spacing order and direction of transcription as in SEQ ID NO: 3:

a gene encoding a repressor protein with the amino acid sequence encoded by open reading frame (ORF) 27, the ribosome binding site (RBS) of ORF 27, the −35 and −10 promoter sequences of P2, the operator sequence O1, the operator sequence O2, the −35 and −10 promoter sequences of P1, a gene encoding a tec protein with the amino acid sequence encoded by ORF 28, the Shine-Dalgarno (SD) sequence of said gene encoding a tec protein, wherein the elements are linked by intervening sequences and optionally flanked by flanking sequences, said intervening sequences and optionally said flanking sequences having the same length as in SEQ ID NO: 3 but not necessarily the same composition.

2. A modification of a complex inducible promoter system according to claim 1, wherein under inducing circumstances or after being subjected to inducing circumstances the expression product of the repressor gene can no longer repress the promoter system, the modification being located in the repressor gene as comprised on plasmid pIR14 and deposited as Lactococcus lactis subsp. cremoris LL302 (pIR14) at Centraal Bureau voor Schimmelcultures in Baarn, The Netherlands in accordance with the Budapest Treaty on May 11, 1995 with accession number CBS 327.95.

3. A recombinant vector comprising a complex inducible promoter system according to claim 1.

4. A transformed lactic acid bacterium, obtainable through transformation with a recombinant vector according to claim 3, said transformed lactic acid bacterium comprising a complex inducible promoter system wherein said transformed lactic acid bacterium is free of the phage sequences normally associated with the promoter system existing in the native phage, which transformed lactic acid bacterium is either the natural host of the phage from which the complex inducible promoter system is obtained, or a different lactic acid bacterium.

5. A transformed lactic acid bacterium according to claim 4, wherein a gene encoding a desired protein is under control of the complex inducible promoter system.

6. A process for the production of a desired protein by a transformed lactic acid bacterium, comprising expressing a gene encoding said desired protein or a precursor thereof under control of a complex inducible promoter system according to claim 1.

7. A process according to claim 6, in which the transformed lactic acid bacterium is food-grade,
wherein food-grade DNA sequences are used and optionally, non-food-grade DNA sequences are removed.

8. A process according to claim 6, wherein the desired protein is secreted by the lactic acid bacterium due to the presence of a DNA sequence fused to the gene encoding the desired protein and effecting secretion of the desired protein or a precursor thereof.

9. A promoter system according to claim 1 comprising as further elements the RBS of ORF 29 and a nucleic acid sequence encoding the amino acid sequence encoded by ORF 29.

10. A promoter system according to claim 1 wherein the gene encoding a repressor protein has the nucleic acid sequence of ORF 27, the gene encoding a protein tec has the nucleic acid sequence of ORF 28 and the promoter system comprises additional elements, said additional elements being a nucleic acid sequence of ORF 29 and the RBS of ORF 29.

11. A promoter system according to claim 1 comprising the DNA sequence SEQ ID NO: 3 downstream from the codon encoding the terminal Ser of tec in ORF 28.

12. A promoter system according to claim 1 further comprising the operator sequence O3 of SEQ ID NO: 3 as an element.

13. A process comprising the process of claim 6 wherein the desired protein is a lysis protein causing lysis of the bacterial cells so that the contents of the cells are released.

14. A process according to claim 13, in which the desired protein is an enzyme involved in flavour formation.

15. A process according to claim 13 or 14, in which the desired protein is a protein having a function in a cheese production process, or an enzyme involved in cheese flavour formation.

16. A process according to claim 15, wherein the protein having a function in a cheese production process is chymosin.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 93 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Lactococcus lactis phage R1-t
      (C) INDIVIDUAL ISOLATE: Fig.1B cds ORF 29 and E.coli lacZ (ix) FEATURE:
      (A) NAME/KEY: CDS
      (B) LOCATION: 1..93

(xi) SEQUENCE DESCRIPTION: SEQ ID NO: 1:

```
ACA ATC CGA AGC ACG GAG TAC ATG ACG GAT GCG AAG CTT GCA TGC CTG     48
Thr Ile Arg Ser Thr Glu Tyr Met Thr Asp Ala Lys Leu Ala Cys Leu
 1               5                  10                  15

CAG GTC GAC TCT AGA GTC GGG GCC GTC GTT TTA CAA CGT CGT GAC         93
Gln Val Asp Ser Arg Val Gly Ala Val Val Leu Gln Arg Arg Asp
             20                  25                  30
```

(2) INFORMATION FOR SEQ ID NO: 2:

(i) SEQUENCE CHARACTERISTICS:
      (A) LENGTH: 31 amino acids
      (B) TYPE: amino acid
      (D) TOPOLOGY: linear (ii) MOLECULE TYPE: protein (xi) SEQUENCE DESCRIPTION: SEQ ID NO: 2:

```
Thr Ile Arg Ser Thr Glu Tyr Met Thr Asp Ala Lys Leu Ala Cys Leu
 1               5                  10                  15

Gln Val Asp Ser Arg Val Gly Ala Val Val Leu Gln Arg Arg Asp
             20                  25                  30
```

(2) INFORMATION FOR SEQ ID NO: 3:

(i) SEQUENCE CHARACTERISTICS:
        (A) LENGTH: 1888 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Lactococcus lactis phage R1-t
        (C) INDIVIDUAL ISOLATE: Fig.2 cds ORF27, ORF 28 and ORF29

(ix) FEATURE:
        (A) NAME/KEY: CDS
        (B) LOCATION: complement (1..336)

(ix) FEATURE:
        (A) NAME/KEY: CDS
        (B) LOCATION: complement (350..590)

(ix) FEATURE:
        (A) NAME/KEY: CDS
        (B) LOCATION: 880..1654

(xi) SEQUENCE DESCRIPTION: SEQ ID NO: 3:

```
AAGCTTCGCA TCCGTCATGT ACTCCGTGCT TCGGATTGTT GGGAGGACTT CTTCATATAC      60

CCAATCCTGA AATGGCTCAG CACTTGGCAA TTTACTTTCG CCAGCTAATT GATAAAGACC     120

AGGTTCTGAA ATTACTGTGA CACTTTGTAC TCCTGAGGGG GTCGTGATTC GCGACTCCCT     180

CTTATATTTG TCTTTTACAT GAGATTTCAA AGCATCCCTG AAATTCTTGT AACCAATAGC     240

AATTGCTACA TCTTTTCCGA CAAACCAAGG TTCATCATTG ATAAGTACTG TTCGTACTGG     300

TAAGTTATTA AAATTAAAAT TTTGTAATTC TTTCATGTTT TGCCTTTCTA ACTAGCCAAT     360

TTGTCAAGTT TTTGATTAAA ATTTTTCAGC ACAAAAATAA CATCGGTTAA ATCTACTCCA     420

ATAACCTCTG CAATGTTCGC TGCTGAAACA GCATCTATTC TAGATGGGTT GATACGCCAC     480

TTATAAAATG TTGTATAGGG AACGTTAATT TTTTTTGCGA TAACTTTATA CTTCATTCCT     540

GAAGAGTCTA ATAACTCATC TAGTGGCTCA TAAGTTTTTT TCTCTGCCAT ACTGGCTCCT     600

TTCTGCCCCT CTGGGGCTTT TTATTTGCCA AACTTGCTAC TTACATCGCG GTGGATACGT     660

CGTGTACCGT CATTTGAGCC TGTTCCGTCC GCCGTACTGA ATGCTCCATG ATTGTTCGCT     720

TGTTTGACTT TATGAATTAA TTATAACCTT AACTATCCAA TTTGTCAAGT TAAAACTTTC     780

CAAATTGACA AGTTTTGTTG TTTGTGCTAT AATTAGTGTA TGAAAAAAAT ACGACTACCT     840

GAAATGATAG ATTATTTCAG AAAAGAGAAT GGTTGGACG ATG AAA GAG TTT GGC       894
                                            Met Lys Glu Phe Gly
                                              1               5

GAA AAG CTA GGA AAA TCT GAG TCA GCT ATT TCG AAA TGG ATA AAA GGG       942
Glu Lys Leu Gly Lys Ser Glu Ser Ala Ile Ser Lys Trp Ile Lys Gly
           10                  15                  20

GTT AGA AGT CCC ATG GTT GAA GAT TTT GAT AAA ATG GTC AAT CTA TTC       990
Val Arg Ser Pro Met Val Glu Asp Phe Asp Lys Met Val Asn Leu Phe
         25                  30                  35

AAT ACT GAT CCT GAG ACA TTA ATG TAT GGT GCT TCT GAC CTT TCT ACA      1038
Asn Thr Asp Pro Glu Thr Leu Met Tyr Gly Ala Ser Asp Leu Ser Thr
 40                  45                  50

ACT CTA TCC GAA ATA AAT AAA ATC AGT TCA CAA CTC GAA GAA CCA CGT      1086
Thr Leu Ser Glu Ile Asn Lys Ile Ser Ser Gln Leu Glu Glu Pro Arg
         55                  60                  65

CAG AAA GTT GTT TTA AAT ACT GCA AAT AAT CAG TTA GAT GAG CAA AAC      1134
```

```
              Gln Lys Val Val Leu Asn Thr Ala Asn Asn Gln Leu Asp Glu Gln Asn
               70                  75                  80                  85

CAA GAA AAG AAA AAG GAA TCT AAA GTG ATT CCA ATT AAT AAA ATA CCT            1182
Gln Glu Lys Lys Lys Glu Ser Lys Val Ile Pro Ile Asn Lys Ile Pro
                 90                  95                 100

GAC GAT TTA CCA CCA TAT ATA AGT AGA AAG ATT TTA GAG AAT TTC GTT            1230
Asp Asp Leu Pro Pro Tyr Ile Ser Arg Lys Ile Leu Glu Asn Phe Val
                    105                 110                 115

ATG CCT ACA AAC ACT ATG GAA TAT GAG GCT GAT GAA GAT ATG GTA GAT            1278
Met Pro Thr Asn Thr Met Glu Tyr Glu Ala Asp Glu Asp Met Val Asp
                120                 125                 130

GTT CCT ATT CTT GGT AGG ATA GCG GCC GGA CTT CCT CTT GAT GCA GTA            1326
Val Pro Ile Leu Gly Arg Ile Ala Ala Gly Leu Pro Leu Asp Ala Val
                135                 140                 145

GAA AAC TTC GAC GGT ACA AGA CCA GTA CCT GCG CAC TTC TTA TCT TCT            1374
Glu Asn Phe Asp Gly Thr Arg Pro Val Pro Ala His Phe Leu Ser Ser
150                 155                 160                 165

GCT CGT GAT TAC TAT TGG TTA ATG GTT GAT GGG CAT AGC ATG GAA CCG            1422
Ala Arg Asp Tyr Tyr Trp Leu Met Val Asp Gly His Ser Met Glu Pro
                    170                 175                 180

AAA ATT CCA TAT GGA GCT TAT GTT TTA ATT GAA GCT GTT CCT GAT GTG            1470
Lys Ile Pro Tyr Gly Ala Tyr Val Leu Ile Glu Ala Val Pro Asp Val
                185                 190                 195

AGC GAC GGT ACT ATT GGA GCT GTT CTT TTC CAT GAT GAT TGT CAG GCA            1518
Ser Asp Gly Thr Ile Gly Ala Val Leu Phe His Asp Asp Cys Gln Ala
                200                 205                 210

ACA TTA AAA AAA GTT TAT CAT GAA ATA GAT TGC TTG AGA CTT GTG TCA            1566
Thr Leu Lys Lys Val Tyr His Glu Ile Asp Cys Leu Arg Leu Val Ser
215                 220                 225

ATC AAC AAA GAA TTT AAA GAC CAA TTT GCT ACA CAA GAC AAT CCA GCA            1614
Ile Asn Lys Glu Phe Lys Asp Gln Phe Ala Thr Gln Asp Asn Pro Ala
230                 235                 240                 245

GCT GTG ATT GGG CAA GCT GTC AAA GTA GAA ATT GAT TTATAATTAA                 1660
Ala Val Ile Gly Gln Ala Val Lys Val Glu Ile Asp Leu
                250                 255

ATATACGAGC AATGTCTTGA TTCTCGTTAA AAGCTAGGTT AGGAAATATA AACATTATGA          1720

AAAATGGAAA AACTCCTAAA GCTAAAAAAC CAATTTATAA AAGAATATGG TTTTGGATTG          1780

TTGTAGTAAT CGTAGTAGCG GTTATTGGTA GCGCACTTGG AGGAGGAGGC AAAGGCAAAA          1840

GTGGAACATC AACTTCTACA TCCTCAAGTT CTAAAATTAA AACAGCTG                      1888

(2) INFORMATION FOR SEQ ID NO: 4:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 4:

Met Lys Glu Leu Gln Asn Phe Asn Phe Asn Asn Leu Pro Val Arg Thr
 1               5                  10                  15

Val Leu Ile Asn Asp Glu Pro Trp Phe Val Gly Lys Asp Val Ala Ile
                20                  25                  30

Ala Ile Gly Tyr Lys Asn Phe Arg Asp Ala Leu Lys Ser His Val Lys
            35                  40                  45

Asp Lys Tyr Lys Arg Glu Ser Arg Ile Thr Thr Pro Ser Gly Val Gln
        50                  55                  60
```

Ser Val Thr Val Ile Ser Glu Pro Gly Leu Tyr Gln Leu Ala Gly Glu
65                   70                  75                  80

Ser Lys Leu Pro Ser Ala Glu Pro Phe Gln Asp Trp Val Tyr Glu Glu
                85                  90                  95

Val Leu Pro Thr Ile Arg Ser Thr Glu Tyr Met Thr Asp Ala Lys Leu
            100                 105                 110

(2) INFORMATION FOR SEQ ID NO: 5:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO: 5:

Met Ala Glu Lys Lys Thr Tyr Glu Pro Leu Asp Glu Leu Leu Asp Ser
1               5                   10                  15

Ser Gly Met Lys Tyr Lys Val Ile Ala Lys Lys Ile Asn Val Pro Tyr
                20                  25                  30

Thr Thr Phe Tyr Lys Trp Arg Ile Asn Pro Ser Arg Ile Asp Ala Val
            35                  40                  45

Ser Ala Ala Asn Ile Ala Glu Val Ile Gly Val Asp Leu Thr Asp Val
50                  55                  60

Ile Phe Val Leu Lys Asn Phe Asn Gln Lys Leu Asp Lys Leu Ala Ser
65                  70                  75                  80

(2) INFORMATION FOR SEQ ID NO: 6:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO: 6:

Met Lys Glu Phe Gly Glu Lys Leu Gly Lys Ser Glu Ser Ala Ile Ser
1               5                   10                  15

Lys Trp Ile Lys Gly Val Arg Ser Pro Met Val Glu Asp Phe Asp Lys
                20                  25                  30

Met Val Asn Leu Phe Asn Thr Asp Pro Glu Thr Leu Met Tyr Gly Ala
            35                  40                  45

Ser Asp Leu Ser Thr Thr Leu Ser Glu Ile Asn Lys Ile Ser Ser Gln
50                  55                  60

Leu Glu Glu Pro Arg Gln Lys Val Val Leu Asn Thr Ala Asn Asn Gln
65                  70                  75                  80

Leu Asp Glu Gln Asn Gln Glu Lys Lys Lys Glu Ser Lys Val Ile Pro
                85                  90                  95

Ile Asn Lys Ile Pro Asp Asp Leu Pro Pro Tyr Ile Ser Arg Lys Ile
            100                 105                 110

Leu Glu Asn Phe Val Met Pro Thr Asn Thr Met Glu Tyr Glu Ala Asp
        115                 120                 125

Glu Asp Met Val Asp Val Pro Ile Leu Gly Arg Ile Ala Ala Gly Leu
    130                 135                 140

Pro Leu Asp Ala Val Glu Asn Phe Asp Gly Thr Arg Pro Val Pro Ala
145                 150                 155                 160

His Phe Leu Ser Ser Ala Arg Asp Tyr Tyr Trp Leu Met Val Asp Gly

```
                165                 170                 175
His Ser Met Glu Pro Lys Ile Pro Tyr Gly Ala Tyr Val Leu Ile Glu
                180                 185                 190

Ala Val Pro Asp Val Ser Asp Gly Thr Ile Gly Ala Val Leu Phe His
                195                 200                 205

Asp Asp Cys Gln Ala Thr Leu Lys Lys Val Tyr His Glu Ile Asp Cys
210                 215                 220

Leu Arg Leu Val Ser Ile Asn Lys Glu Phe Lys Asp Gln Phe Ala Thr
225                 230                 235                 240

Gln Asp Asn Pro Ala Ala Val Ile Gly Gln Ala Val Lys Val Glu Ile
                245                 250                 255

Asp Leu (2) INFORMATION FOR SEQ ID NO: 7:

(i) SEQUENCE CHARACTERISTICS:
        (A) LENGTH: 210 amino acids
        (B) TYPE: amino acid
        (D) TOPOLOGY: linear (ii) MOLECULE TYPE: protein (vi) ORIGINAL SOURCE:
        (A) ORGANISM: Escherichia coli phage 434
        (B) STRAIN: CI repressor protein
        (C) INDIVIDUAL ISOLATE: Fig.3 CI434 a.a. sequence (xi) SEQUENCE DESCRIPTION: SEQ ID NO: 7:

Met Ser Ile Ser Ser Arg Val Lys Ser Lys Arg Ile Gln Leu Gly Leu
1               5                   10                  15

Asn Gln Ala Glu Leu Ala Gln Lys Val Gly Thr Thr Gln Gln Ser Ile
                20                  25                  30

Glu Gln Leu Glu Asn Gly Lys Thr Lys Arg Pro Arg Phe Leu Pro Glu
            35                  40                  45

Leu Ala Ser Ala Leu Gly Val Ser Val Asp Trp Leu Leu Asn Gly Thr
50                  55                  60

Ser Asp Ser Asn Val Arg Phe Val Gly His Val Glu Pro Lys Gly Lys
65                  70                  75                  80

Tyr Pro Leu Ile Ser Met Val Arg Ala Gly Ser Trp Cys Glu Ala Cys
                85                  90                  95

Glu Pro Tyr Asp Ile Lys Asp Ile Asp Glu Trp Tyr Asp Ser Asp Val
                100                 105                 110

Asn Leu Leu Gly Asn Gly Phe Trp Leu Lys Val Glu Gly Asp Ser Met
            115                 120                 125

Thr Ser Pro Val Gly Gln Ser Ile Pro Glu Gly His Met Val Leu Val
        130                 135                 140

Asp Thr Gly Arg Glu Pro Val Asn Gly Ser Leu Val Val Ala Lys Leu
145                 150                 155                 160

Thr Asp Ala Asn Glu Arg Thr Phe Lys Lys Leu Val Ile Asp Gly Gly
                165                 170                 175

Gln Lys Tyr Leu Lys Gly Leu Asn Pro Ser Trp Pro Met Thr Pro Ile
            180                 185                 190

Asn Gly Asn Cys Lys Ile Ile Gly Val Val Val Glu Ala Arg Val Lys
        195                 200                 205

Phe Val
    210
```

```
(2) INFORMATION FOR SEQ ID NO: 8:

(i) SEQUENCE CHARACTERISTICS:
        (A) LENGTH: 205 amino acids
        (B) TYPE: amino acid
        (D) TOPOLOGY: linear (ii) MOLECULE TYPE: protein (vi) ORIGINAL SOURCE:
        (A) ORGANISM: Bacillus subtilis
        (B) STRAIN: DinR protein
        (C) INDIVIDUAL ISOLATE: Fig.3 DinR a.a. sequence (xi) SEQUENCE DESCRIPTION: SEQ ID NO: 8:

Met Thr Lys Leu Ser Lys Arg Gln Leu Asp Ile Leu Arg Phe Ile Lys
1               5                   10                  15

Ala Glu Val Lys Ser Lys Gly Tyr Pro Pro Ser Val Arg Glu Ile Gly
                20                  25                  30

Glu Ala Val Gly Leu Ala Ser Ser Ser Thr Val His Gly His Leu Ala
            35                  40                  45

Arg Leu Glu Thr Lys Gly Leu Ile Arg Arg Asp Pro Thr Lys Pro Arg
        50                  55                  60

Ala Ile Glu Ile Leu Asp Glu Val Asp Ile Pro Gln Ser Gln Val
65                  70                  75                  80

Val Asn Val Pro Val Ile Gly Lys Val Thr Ala Gly Ser Pro Ile Thr
                85                  90                  95

Ala Val Glu Asn Ile Glu Glu Tyr Phe Pro Leu Pro Asp Arg Met Val
            100                 105                 110

Pro Pro Asp Glu His Val Phe Met Leu Glu Ile Met Gly Asp Ser Met
        115                 120                 125

Ile Asp Ala Gly Ile Leu Asp Lys Asp Tyr Val Ile Val Lys Gln Gln
130                 135                 140

Asn Thr Ala Asn Asn Gly Glu Ile Val Val Ala Met Thr Glu Asp Asp
145                 150                 155                 160

Glu Ala Thr Val Lys Arg Phe Tyr Lys Glu Asp Thr His Ile Arg Leu
                165                 170                 175

Gln Pro Glu Asn Pro Thr Met Glu Pro Ile Ile Leu Gln Asn Val Ser
            180                 185                 190

Ile Leu Gly Lys Val Ile Gly Val Phe Arg Thr Val His
        195                 200                 205

(2) INFORMATION FOR SEQ ID NO: 9:

(i) SEQUENCE CHARACTERISTICS:
        (A) LENGTH: 20 amino acids
        (B) TYPE: amino acid
        (D) TOPOLOGY: linear (ii) MOLECULE TYPE: protein (vi) ORIGINAL SOURCE:
        (A) ORGANISM: Escherichia coli phage phi80
        (C) INDIVIDUAL ISOLATE: Fig.4 phi80 gp30 partial a.a.
            sequence (xi) SEQUENCE DESCRIPTION: SEQ ID NO: 9:

His Lys Val Leu Ala Glu Lys Val Gly Val Thr Pro Gln Gln Ala Ile
1               5                   10                  15

Asn Met Leu Lys
            20
```

-continued (2) INFORMATION FOR SEQ ID NO: 10:

(i) SEQUENCE CHARACTERISTICS:
        (A) LENGTH: 20 amino acids
        (B) TYPE: amino acid
        (D) TOPOLOGY: linear (ii) MOLECULE TYPE: protein (vi) ORIGINAL SOURCE:
        (A) ORGANISM: Escherichia coli phage lambda CII
        (C) INDIVIDUAL ISOLATE: Fig.4 lambda CII partial a.a.
            sequence (xi) SEQUENCE DESCRIPTION: SEQ ID NO: 10:

```
Thr Glu Lys Thr Ala Glu Ala Val Gly Val Asp Lys Ser Gln Ile Ser
1               5                  10                  15

Arg Trp Lys Arg
            20
```

(2) INFORMATION FOR SEQ ID NO: 11:

(i) SEQUENCE CHARACTERISTICS:
        (A) LENGTH: 20 amino acids
        (B) TYPE: amino acid
        (D) TOPOLOGY: linear (ii) MOLECULE TYPE: protein (vi) ORIGINAL SOURCE:
        (A) ORGANISM: Escherichia coli phage P22
        (C) INDIVIDUAL ISOLATE: Fig.4 P22 C2 partial a.a. sequence (xi) SEQUENCE DESCRIPTION: SEQ ID NO: 11:

```
Gln Ala Ala Leu Gly Lys Met Val Gly Val Ser Asn Val Ala Ile Ser
1               5                  10                  15

Gln Trp Glu Arg
            20
```